(12) United States Patent
Feng et al.

(10) Patent No.: US 7,837,847 B2
(45) Date of Patent: Nov. 23, 2010

(54) HIGH PURITY WATER PH SENSOR WITH SHIELDED FLOWING LIQUID JUNCTION

(75) Inventors: Chang-Dong Feng, Long Beach, CA (US); Beth M. Covey, Tustin, CA (US); Wayne B. Wood, Silverado, CA (US)

(73) Assignee: Rosenmount Analytical Inc., Irvine, CA (US)

( * ) Notice: Subject to any disclaimer, the term of this patent is extended or adjusted under 35 U.S.C. 154(b) by 245 days.

(21) Appl. No.: 11/904,620

(22) Filed: Sep. 27, 2007

(65) Prior Publication Data

US 2008/0237042 A1 Oct. 2, 2008

Related U.S. Application Data

(60) Provisional application No. 60/848,772, filed on Oct. 2, 2006.

(51) Int. Cl.
*G01N 27/30* (2006.01)
*G01N 27/401* (2006.01)
*G01N 27/403* (2006.01)
*G01N 27/36* (2006.01)

(52) U.S. Cl. .................. 204/433; 204/416; 204/435; 204/412; 204/400; 205/787.5

(58) Field of Classification Search ......... 204/416–420, 204/433, 436, 435; 205/787.5
See application file for complete search history.

(56) References Cited

U.S. PATENT DOCUMENTS

| | | | |
|---|---|---|---|
| 3,208,927 A | 9/1965 | Arthur et al. | |
| 3,492,216 A | 1/1970 | Riseman et al. | |
| 3,862,895 A | 1/1975 | King et al. | 204/195 |
| 4,390,406 A | 6/1983 | Kato et al. | 204/435 |
| 4,571,298 A | 2/1986 | Holz | 210/498 |
| 4,667,939 A | 5/1987 | Luyckx | 266/287 |
| 4,822,456 A * | 4/1989 | Bryan | 205/789 |

(Continued)

FOREIGN PATENT DOCUMENTS

EP 1 610 120 A1 12/2005

(Continued)

OTHER PUBLICATIONS

International Search Report and Written Opinion from International Application No. PCT/US2007/020821, filed Sep. 27, 2007.

(Continued)

*Primary Examiner*—Alexa D Neckel
*Assistant Examiner*—Jennifer Dieterle
(74) *Attorney, Agent, or Firm*—Christopher R. Christenson; Westman, Champlin & Kelly, P.A.

(57) ABSTRACT

A pH sensor is provided. The pH sensor includes a body, a glass electrode, a reference electrode and a solution ground. The glass electrode is disposed on the body to contact a liquid sample. The reference electrode has a reference fill solution disposed within the body. The solution ground electrode is operably coupled to the body and has a portion of the solution ground electrode that is disposed within a harbor such that a portion of the solution ground electrode is configured to contact the liquid sample. The body has a passageway that extends from the reference fill solution to an aperture proximate the liquid sample.

10 Claims, 5 Drawing Sheets

U.S. PATENT DOCUMENTS

| | | | |
|---|---|---|---|
| 5,008,008 A | 4/1991 | Lockshaw | 210/167.12 |
| 5,139,641 A | 8/1992 | Neukum | 204/435 |
| 5,469,070 A | 11/1995 | Koluvek | 324/713 |
| 5,830,338 A | 11/1998 | Seto et al. | 204/416 |
| 6,022,474 A | 2/2000 | MacKelvie | 210/170.01 |
| 6,322,680 B1 * | 11/2001 | Itsygin | 204/416 |
| 6,495,012 B1 | 12/2002 | Fletcher et al. | 204/435 |
| 6,551,480 B1 | 4/2003 | Taagaard et al. | 204/435 |
| 2003/0029722 A1 | 2/2003 | Erdosy et al. | 204/435 |
| 2004/0011670 A1 * | 1/2004 | Broadley et al. | 205/775 |
| 2004/0195098 A1 | 10/2004 | Broadley et al. | 204/435 |
| 2006/0278529 A1 | 12/2006 | Feng et al. | 204/435 |

FOREIGN PATENT DOCUMENTS

| | | |
|---|---|---|
| GB | 2 341 235 | 3/2000 |
| WO | WO 03/052387 A2 | 6/2003 |

OTHER PUBLICATIONS

"Theory and Practice of pH Measurement," Rosemount Analytical Inc., Sep. 1999.

International Search Report and Written Opinion from application No. PCT/US2006/022418, filed Jun. 8, 2006.

* cited by examiner

US 7,837,847 B2

HIGH PURITY WATER PH SENSOR WITH SHIELDED FLOWING LIQUID JUNCTION

CROSS-REFERENCE TO CO-PENDING APPLICATION

The present application is based on and claims the benefit of U.S. provisional patent application Ser. No. 60/848,772, filed Oct. 2, 2006, the content of which is hereby incorporated by reference in its entirety.

BACKGROUND

Electrochemical cells form the basis of a variety of analytical sensors. Electrochemical cells generally have two or more electrodes of the cell and are coupled to an analyzer that measures an electrical characteristic of the cell in order to infer a property of a sample within, or otherwise coupled to, the cell. Many electrochemical cells include a measurement electrode and a reference electrode. The reference electrode will generally include a chamber that houses a reference electrode fill solution. A junction, of some sort, allows electrochemical interaction between a sample solution and the fill solution. Electrochemical cells can be used for oxidation/reduction potential (ORP) sensors, pH sensors, or other suitable sensors.

One type of junction used with reference electrodes of electrochemical cells is known as a liquid junction. A liquid junction uses a relatively small passageway that is in fluidic communication with both the sample solution and the reference fill solution. In order to achieve a stable potential at the liquid junction, it is generally preferred that at least some flow of reference fill solution through the passageway into the sample solution be induced. With a "flowing" liquid junction, the reference electrode fill solution constantly flows through the liquid junction into the sample solution.

As demands for pH measurement of high purity water increase, new sources of error that were previously unknown or misunderstood must be addressed. Providing a pH sensing system for high purity water applications that is able to provide increased accuracy and/or precision would benefit the art of process analytic sensing.

SUMMARY

A pH sensor is provided. The pH sensor includes a body, a glass electrode, a reference electrode and a solution ground. The glass electrode is disposed on the body to contact a liquid sample. The reference electrode has a reference fill solution disposed within the body. The solution ground electrode is operably coupled to the body and has a portion of the solution ground electrode that is disposed within a harbor such that a portion of the solution ground electrode is configured to contact the liquid sample. The body has a passageway that extends from the reference fill solution to an aperture proximate the liquid sample.

DETAILED DESCRIPTION

Embodiments of the present invention generally take advantage of a new appreciation for a source of error in the sensing of pH for high purity water applications. In order to better understand the various solutions provided in accordance with embodiments of the present invention, it is helpful first to understand the manner by which this appreciation of the problem occurs.

One challenge for measurement of pH in high purity water is the elimination of the junction potential at the reference electrode. The junction potential is generated by the difference in mobility between cations and anions at the reference junction. To eliminate the junction potential, a common approach is to adapt a flowing junction with the reference electrolyte flowing through it continuously. Electrolytic cells with flowing liquid junctions are known. For example, United States Patent Application 2006/0278529 A1 discloses an electrochemical cell with an improved flowing liquid junction. Generally, a pH sensor with a flowing liquid junction can reach an accuracy of 0.05 pH.

A new high purity sensor under development utilizes a laser-drilled capillary as the flowing junction with a potassium chloride (KCl) solution having a concentration of 1M flowing through the capillary during operation. The sensor consists of a pH glass electrode, an Ag/AgCl reference electrode with the capillary flowing junction, and a stainless steel electrode as the solution ground. This sensor was tested in a sample flow cell with high purity water flowing therethrough. The pH value of the high purity water was adjusted and held constant by injecting a small amount of ammonia ($NH_3$) into the sample stream. The amount of ammonia injected was monitored by a conductivity measurement. The sensor output during the high purity water test was coupled to commercially available analyzer sold under the trade designation Model 1055 SOLU COMP II™ Dual Input pH/ORP/conductivity/resistivity Analyzer, available from Rosemount Analytical Inc., of Irvine, Calif. The sample flow rate was approximately 1 gallon per hour (GPH), and the conductivity of the sample water after ammonia injection was 0.61 µS.

Figure 1:
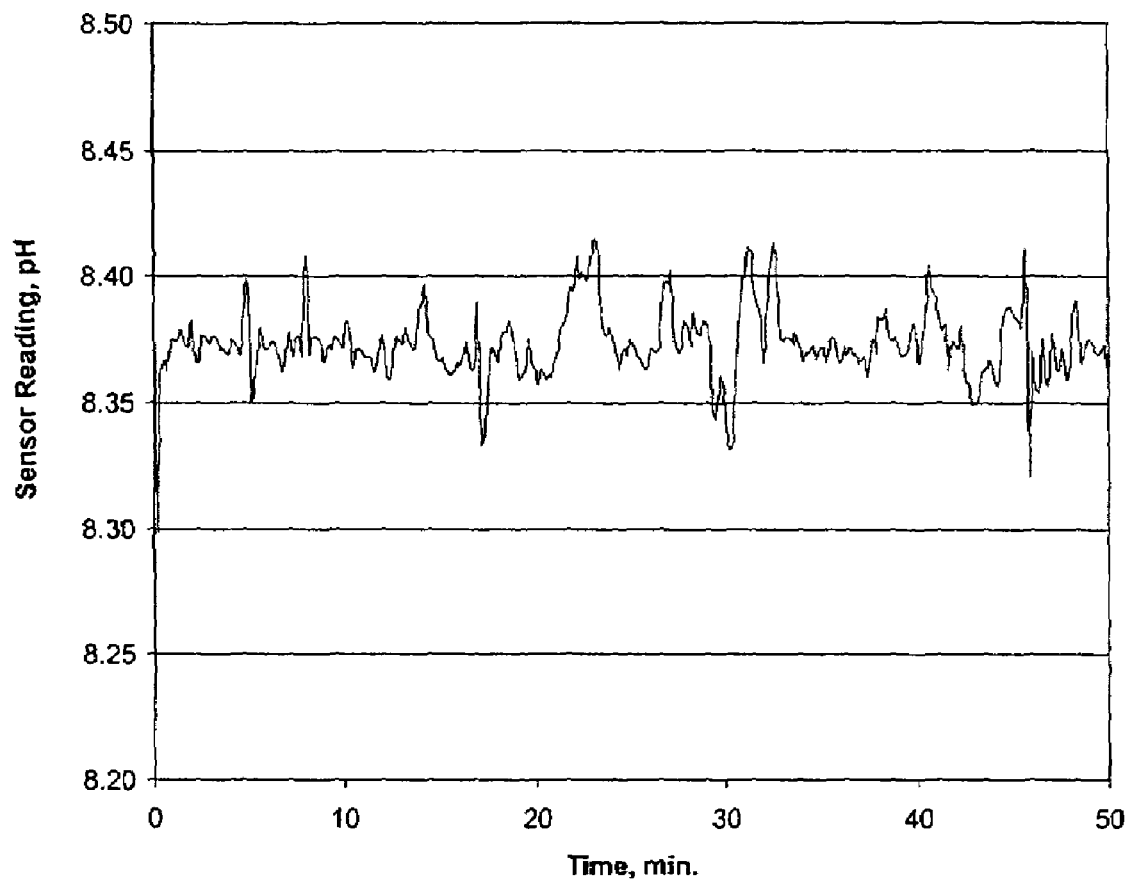
FIG. 1 is a chart illustrating a pH from a prior art pH sensor over time.
Figure 2:
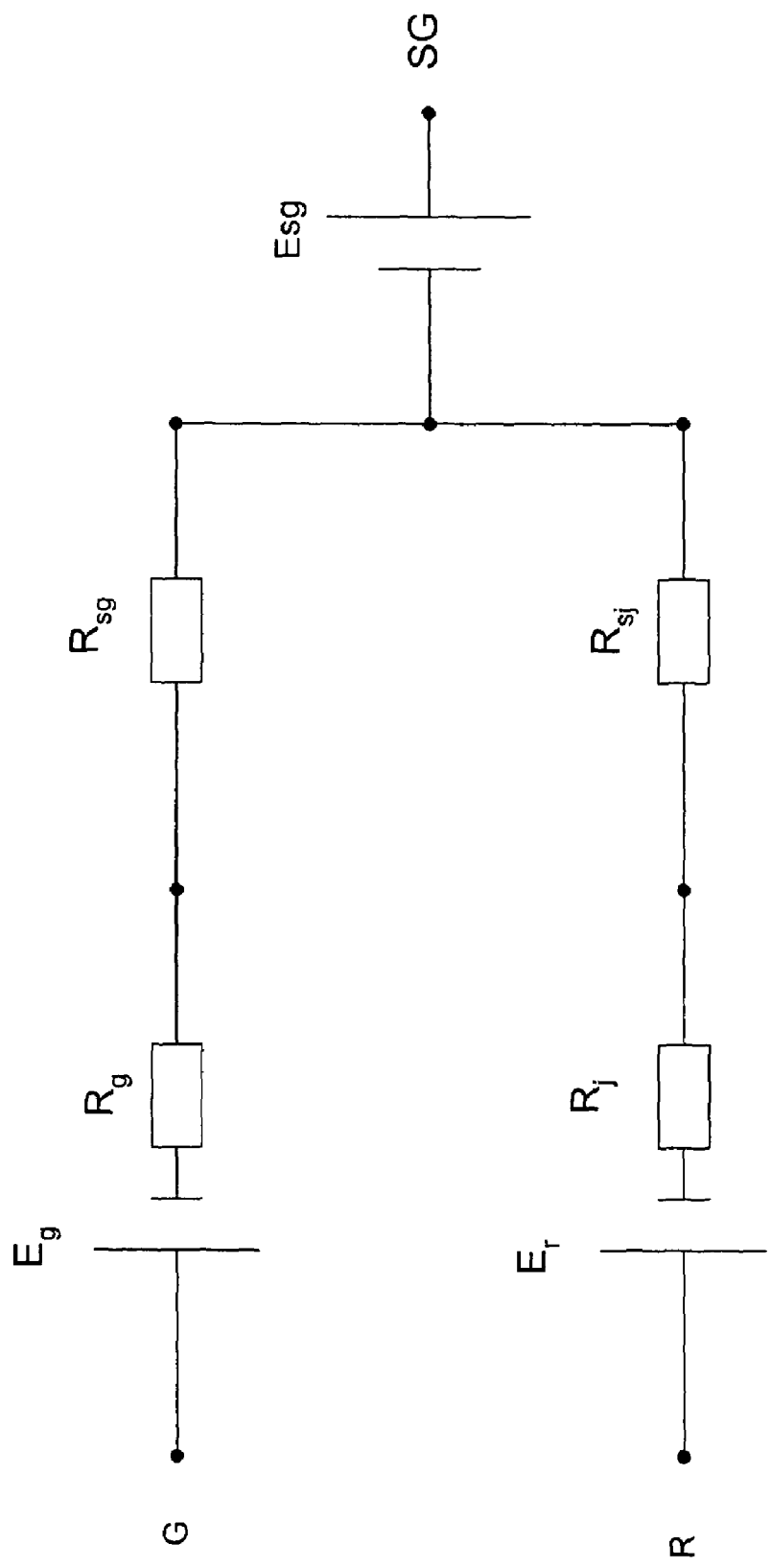
FIG. 2 is a simplified equivalent circuit of a pH sensor.

FIG. 1 is a chart illustrating the measured pH from the sensor over time. As shown in FIG. 1, the sensor reading is somewhat noisy, and the noise level is larger than 0.05 pH which is about 3 millivolts. Investigation into the noise, and specifically the individual noise events that occurred during the test, indicated that the noise was caused by unstable conductivity between the capillary flowing junction and the stainless steel solution ground. When the 1 M KCl in the reference electrode of the pH sensor continuously flows out of the capillary into the high purity water sample, it changes the conductivity of the water sample. Depending on the flow pattern in the sample cell, the conductivity between the capillary and the solution ground becomes unstable. The following description explains why the unstable conductivity caused the pH reading noise of the sensor. Like the Model 1055 Analyzer used for the test, most current process pH analyzers have a diagnostic function to detect the failure of a pH sensor during operation. Examples of such failure include a cracked pH bulb and/or a blocked reference junction. FIG. 2 is a simplified equivalent circuit of a pH sensor. Eg, Er, and Esg represent the potential at the glass, reference, and solution ground electrodes, respectively. Rsg and Rsj represent the resistance between the solution ground and the glass electrode, and that between the solution ground and the reference junction, respectively. During the pH measurement, the 1055 circuit uses terminal SG (solution ground) as a common and injects a constant current through terminals G (glass electrode) and R (reference electrode) in the following sequence.

At time 0-200 milliseconds, the analyzer circuit injects current $i_r$ through the reference electrode and does not inject any current through the glass electrode;

At time 200-400 milliseconds, the analyzer circuit does not inject any current through the reference electrode and injects current $-i_g$ through the glass electrode;

At time 400-600 milliseconds, the analyzer circuit injects current $-i_r$ through the reference electrode, and does not inject any current through the glass electrode; and At time 600-800 milliseconds, no current is injected through the reference electrode and current $i_g$ is injected through the glass electrode.

The analyzer circuit then monitors the voltage Vg of terminal G and the voltage Vr of terminal R. By using the equivalent circuit and Ohm's law, Vg and Vr during the positive ($Vg^+$, $Vr^+$) and negative ($Vg^-$, $Vr^-$) current injection can be expressed as:

$$Vr^+ = E_r + E_{sg} + i_r(R_j + R_{sj}^+) \qquad (1);$$

$$Vg^- = E_g + E_{sg} - i_g R_g \qquad (2);$$

$$Vr^- = E_r + E_{sg} - i_r(R_j + R_{sj}^-) \qquad (3); \text{ and}$$

$$Vg^+ = E_g + E_{sg} + i_g R_g \qquad (4).$$

To get the pH signal (Eg–Er) the analyzer executes the following arithmetic operation:

$$[(Vg^+ + Vg^-) - (Vr^+ + Vr^-)]/2 \qquad (5).$$

According to equations 1-4, equation 5 will have the value of:

$$E_g - E_r - i_r(R_{sj}^+ - R_{sj}^-)/2 \qquad (6).$$

From equation 6, it becomes clear that only when $R_{sj}$ stays constant during the current injection, (i.e. $R_{sj}^+ = R_{sj}^-$), the sensor will give a pure pH signal (Eg–Er). If $R_{sj}$ changes due to the water flow pattern in the sample flow cell, the sensor signal will suffer from a noise caused by the $i_r(R_{sj}^+ - R_{sj}^-)/2$ as shown in equation 6. To eliminate the change of $R_{sj}$, a new sensor design in accordance with embodiments of the present invention is used. A safe harbor is added to the pH sensor to protect the area between the capillary junction and the solution ground from flow in the sample cell.

Figure 3:
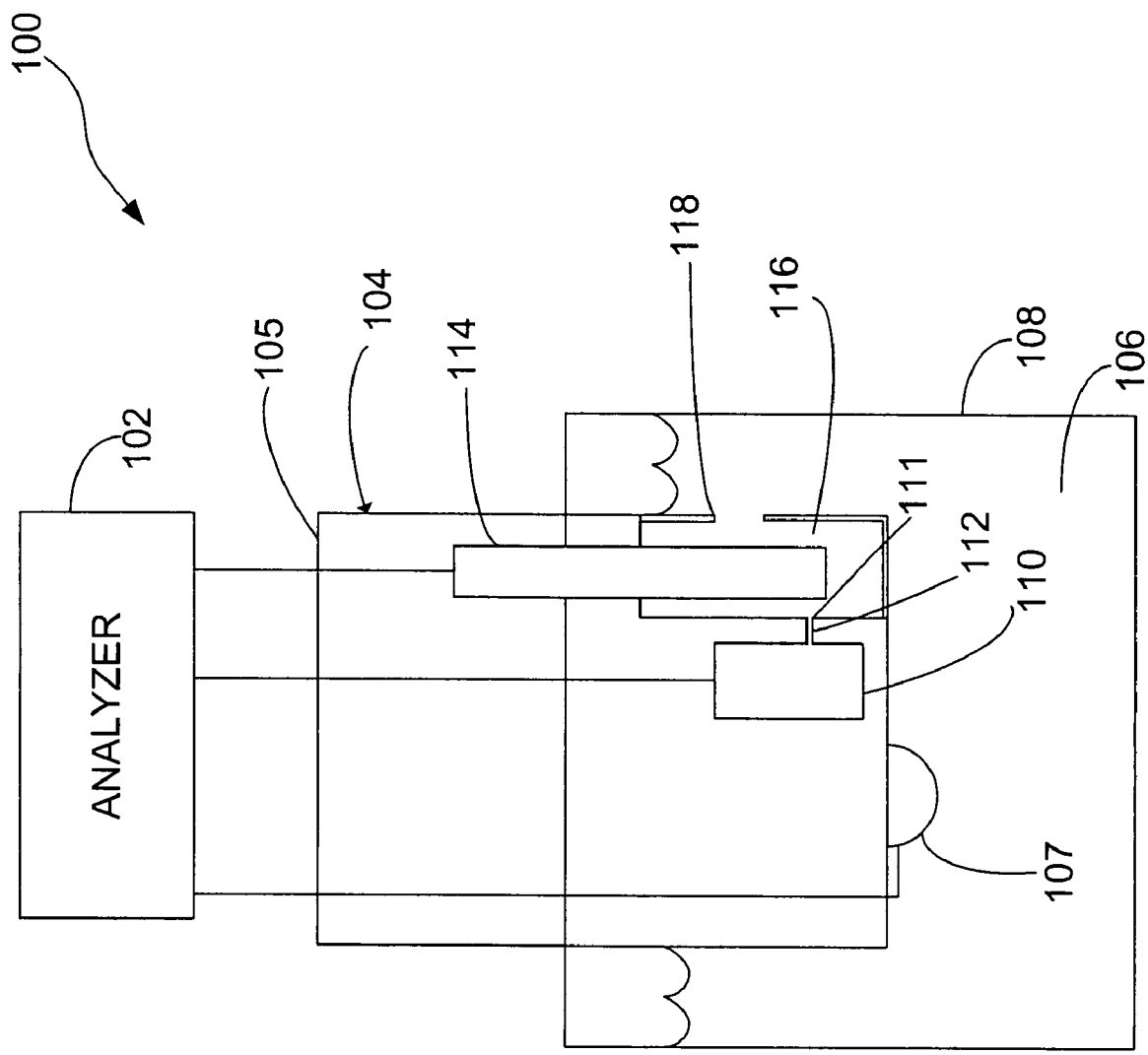
FIG. 3 is a cross-sectional view of a pH sensing system in accordance with an embodiment of the present invention.

FIG. 3 is a diagrammatic view of a pH sensing system in accordance with an embodiment of the present invention. System 100 includes analyzer 102, which can be any suitable analyzer that is able to generate sufficient signals through the pH sensor 104. Sensor 104 is disposed within sample solution 106 and container 108. Sensor 104 includes body 105 and glass electrode 107 disposed thereon. Glass electrode 107 is operably coupled to analyzer 102 and is preferably a known glass bulb electrode, but any suitable electrode design can be used. Body 105 also includes a reference solution reservoir 110, flowing capillary junction 112, solution ground electrode 114 and safe harbor 116. Body 105 can be formed of any suitable material. Suitable examples of materials for body 105 include chemically-resistant, non-conductive polymers, as well as some metals. In embodiments where body 105 is metallic, the various electrodes are electrically isolated from body 105. Reference solution reservoir 110 can be filled with any suitable liquid, such as a potassium chloride solution with a concentration of 1 M. However, those skilled in the art will appreciate other suitable materials that can be used for the reference fill solution. Additionally, other concentrations of the reference fill fluid can be used in accordance with embodiments of the present invention. Capillary 112 is a small conduit that is preferably laser-drilled. While capillary 112 is illustrated as a straight passageway, that is merely one design choice, and various other designs including a circuitous passageway are contemplated. Capillary 112 fluidically couples reference solution reservoir to liquid sample 106 disposed within harbor 116 by way of aperture 111. Solution ground 114 is preferably a stainless steel electrode, but any suitable material can be used. As illustrated in FIG. 3, sensor 104 includes safe harbor 116 which essentially provides an opening 118 to liquid sample 106 and shields the liquid within the harbor 116 from bulk flow that the rest of the liquid sample may undergo.

In one embodiments additional shielding may be provided by placing solution ground electrode 114 such that it obstructs sample solution flow from flowing directly at capillary 112. However, it is believed that using safe harbor 116 to create a volume of liquid sample that is substantially isolated from the rest of liquid sample 106 outside sensor 104, will reduce the fluidic currents proximate aperture 111.

Figure 4:
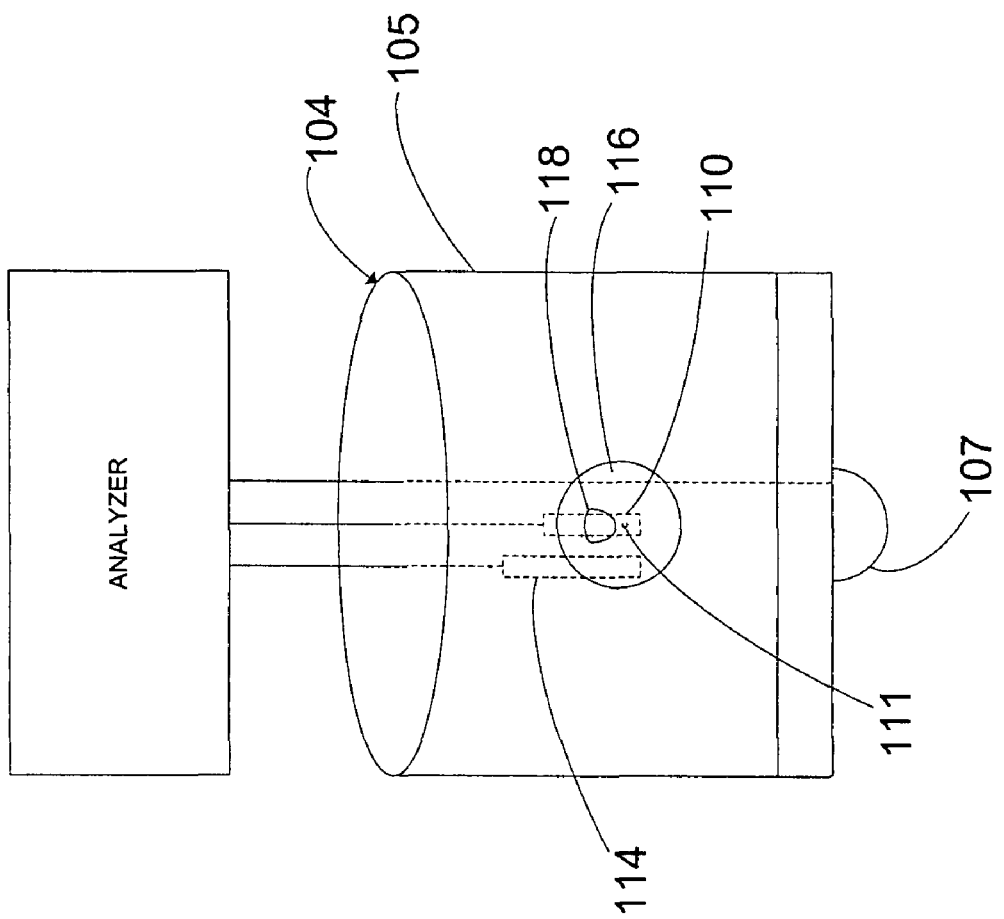
FIG. 4 is a diagrammatic view of a pH sensing system in accordance with an embodiment of the present invention.

FIG. 4 is a diagrammatic view of a pH sensing system in accordance with an embodiment of the present invention. Body 105 defines safe harbor 116 therein. Opening 118 allows liquid sample 106 to flow into harbor 116. However, the liquid sample within harbor 116 will generally not undergo the same bulk fluid movements as liquid sample outside of harbor 116. In this manner, harbor 116 calms the liquid sample proximate aperture 11 of passageway 112.

Figure 5:
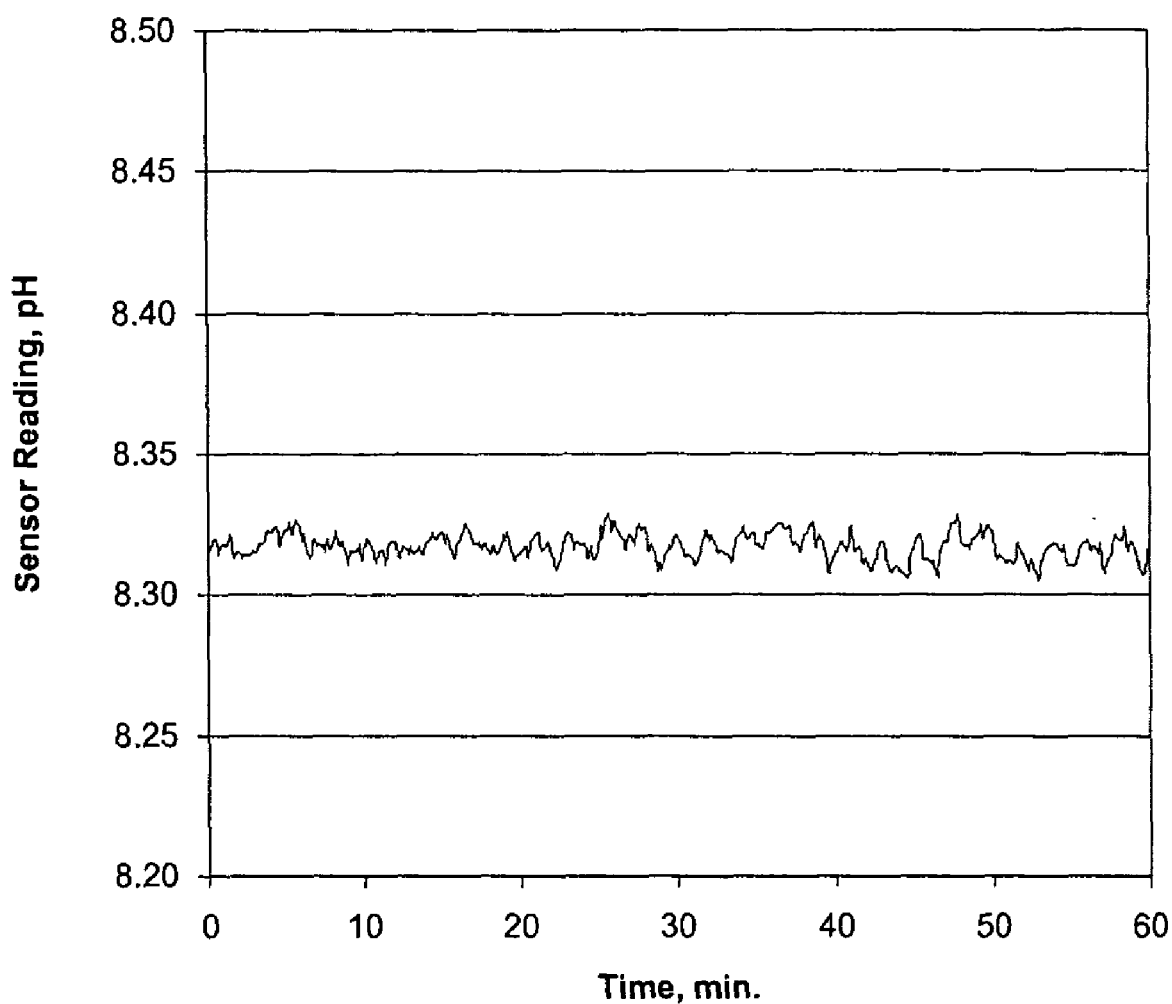
FIG. 5 is a chart of pH versus time for a high purity water test performed using an pH sensor in accordance with an embodiment of the present invention.

FIG. 5 is a chart of pH versus time for a high purity water pH test similar to that shown with respect to FIG. 1. The test illustrated in FIG. 5 employed a pH sensor in accordance with embodiments of the present invention. The pH sensor was coupled to a Model 1055 Analyzer, much the same as the test shown with respect to FIG. 1. Similarly, the sample flow rate was 1 gallon per hour, and the conductivity of the sample water after the ammonia injection was 0.61 μS. By comparing FIGS. 5 and 1, it is clear that a pH sensor for high purity water sensing that includes a safe harbor design has significantly lower noise, and accordingly higher precision than prior sensors.

Although the present invention has been described with reference to preferred embodiments, workers skilled in the art will recognize that changes may be made in form and detail without departing from the spirit and scope of the invention.

What is claimed is:

1. A pH sensor comprising:
    a body having a harbor configured to shield liquid sample within the harbor from bulk liquid sample flow and a harbor opening allowing liquid sample into the harbor;
    a glass electrode disposed outside of the harbor on the body to contact a liquid sample;
    a reference electrode having a reference fill solution disposed within the body;
    a solution ground electrode operably coupled to the body and having a portion of the solution ground electrode disposed within a portion of the harbor such that a portion of the solution ground electrode is configured to contact the liquid sample; and
    wherein the body includes a capillary flowing junction extending from the reference fill solution to an aperture proximate the liquid sample within the harbor.

2. The pH sensor of claim 1, wherein the solution ground electrode is formed of stainless steel.

3. The pH sensor of claim 1, wherein the glass electrode is a glass bulb electrode.

4. The pH sensor of claim 1, wherein the solution ground electrode is interposed between the harbor opening and the reference electrode capillary flowing junction.

5. The pH sensor of claim 1, wherein the capillary flowing junction is a laser-drilled passageway.

6. The pH sensor of claim 5, wherein the capillary flowing junction is a straight passageway.

7. The pH sensor of claim 1, wherein the reference fill solution is potassium chloride.

8. The pH sensor of claim 7, wherein the reference fill solution has a concentration of about 1M.

9. The pH sensor of claim 1, wherein the harbor opening is provided in a sidewall of the body.

10. The pH sensor of claim 9, wherein the solution ground electrode is interposed between the harbor opening and the reference electrode capillary flowing junction.

* * * * *